United States Patent [19]

Brethon et al.

[11] 4,370,555
[45] Jan. 25, 1983

[54] DEVICE FOR STORING A SOURCE OF PHOTONS AND FOR IRRADIATING A BODY BY THE RADIATION FROM SAID SOURCE

[75] Inventors: Jean-Pierre Brethon, Orsay; Jean-Paul Guiho, Le Mesnil St. Denis; Gérard Taniel, Les Essarts le Roi; Georges Viel, Orsay, all of France

[73] Assignees: Commissariat a l'Energie Atomique, Paris; Societe CGR-MeV, Buc, both of France

[21] Appl. No.: 149,927

[22] Filed: May 14, 1980

[30] Foreign Application Priority Data

Nov. 14, 1978 [FR] France ............................... 78 32123

[51] Int. Cl.³ ............................................. G21F 5/02
[52] U.S. Cl. ................................. 378/120; 250/496.1; 250/227
[58] Field of Search ............................. 250/496, 497

[56] References Cited

U.S. PATENT DOCUMENTS

| 2,872,586 | 2/1959 | Papanek | 250/496 |
|---|---|---|---|
| 2,889,464 | 6/1959 | Ruehle | 250/497 |
| 2,951,162 | 8/1960 | Stein | 250/497 |
| 3,025,402 | 3/1962 | Berger et al. | 250/497 |
| 3,073,960 | 1/1963 | Guenther et al. | 250/497 |
| 3,085,157 | 4/1953 | Ginsburgh et al. | 250/497 |
| 3,175,086 | 3/1965 | Johns | 250/497 |

Primary Examiner—Harold A. Dixon
Attorney, Agent, or Firm—Michael N. Meller; Anthony H. Handal

[57] ABSTRACT

A device for storing a source of photons and for irradiating a body by the radiation from said source, comprising
a body for biological protection provided with a cylindrical cavity of circular section and two so-called first and second passages respectively, these passages opening at one and the other of their ends in said cavity and on the outer wall of the body,
a disc for biological protection, whose shape is complementary of that of the cavity of the body and presenting, on the one hand, a housing centered on an axis perpendicular to the axis of the cavity, this housing opening out on the side wall of the disc,
a source of Y radiation contained in said housing,
a precollimator disposed at right angles to said first passage,
means for rotating said disc between a first position for which said source is opposite the precollimator and a second position for which the source is in stored position.

9 Claims, 7 Drawing Figures

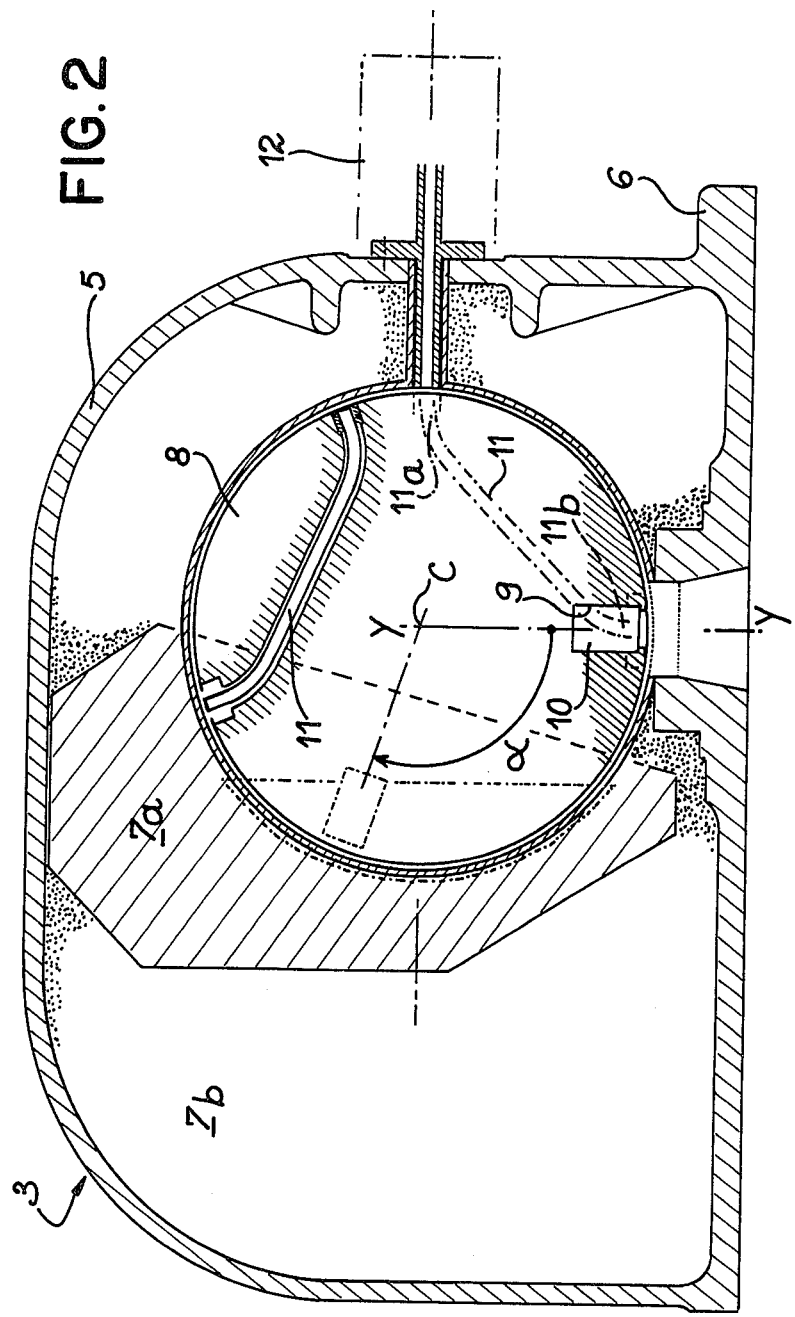

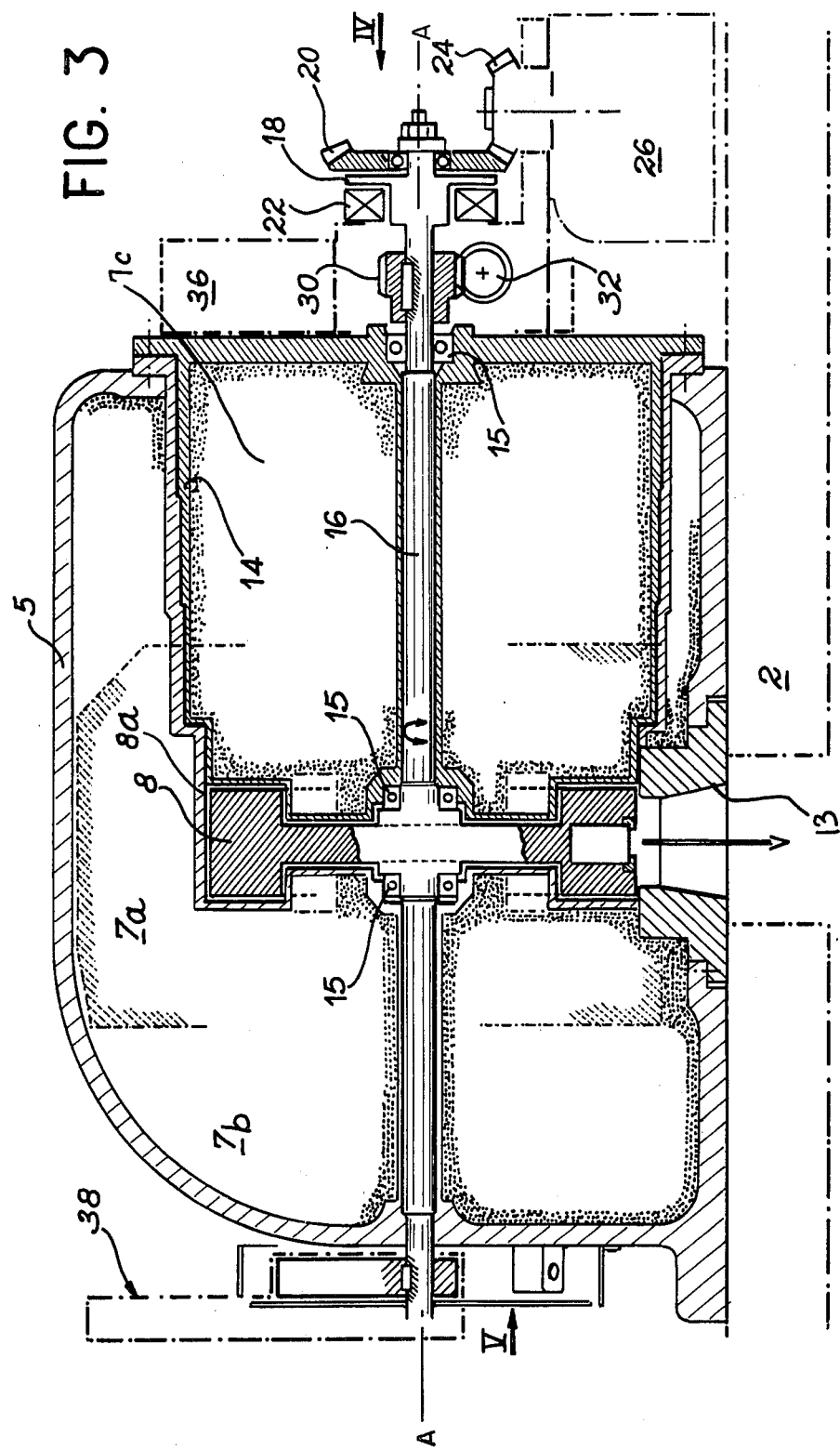

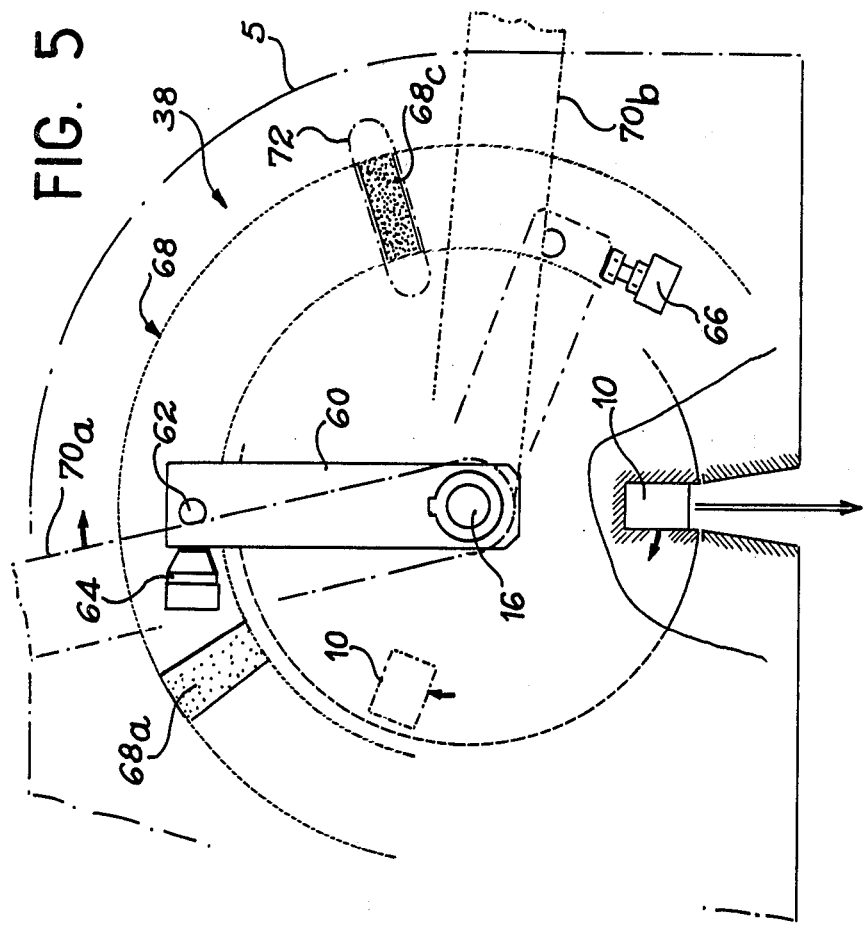
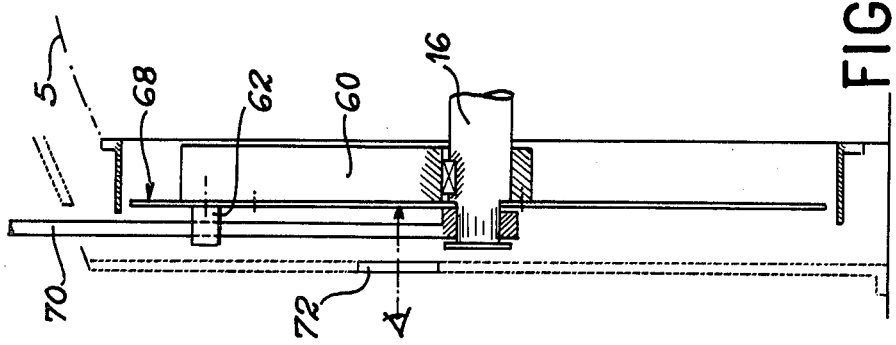

DEVICE FOR STORING A SOURCE OF PHOTONS AND FOR IRRADIATING A BODY BY THE RADIATION FROM SAID SOURCE

The present invention relates to a device for storing a source of γ photons and for irradiating a body by the radiation from said source. The device is applicable to human and veterinary therapy, to metrology, biology, particularly in research, to medicine and to veterinary research.

The invention also relates to a process for transporting and replacing a radioactive source in an irradiation device.

More precisely, the invention relates to a device of the type comprising a body for biological protection, a disc element for supporting a source of photons, movable in said body between a first position allowing the source to be stored under good conditions of biological protection and a second position allowing a beam of photons to be emitted outside the body, a pre-collimator for limiting the beam to a given zone of the irradiated body. For certain applications, such as for example telecobaltotherapy, the device according to the invention further comprises an optical assembly for producing a light beam simulating the beam of photons and a secondary collimation device.

Devices of the above-mentioned type, designed prior to the present invention, are known, which comprise an element for supporting a source of photons, which is mobile in translation, and an optical assembly constituted by a source of light, such as a light bulb, which is carried by the source-supporting element.

U.S. Pat. No. 2,951,162 particularly discloses devices which comprise a metal shell offering biological protection against the radiation of a radioactive source, inside which is located a cylinder rotating about its longitudinal axis. This cylinder comprises two diametrically opposite longitudinal holes. The radioactive source is mounted on a removable bar acting as biological protection and engaging in one of said longitudinal holes. A light source mounted on a similar bar engages in the second longitudinal hole. The protective shell comprises a conical opening for the passage of the radiation from the source and that of the light beam.

Such known devices present a certain number of drawbacks. In particular, they are heavy and of relatively large dimensions. This leads to an unbalance which is undesirable in the case of certain applications for which the irradiation device is subjected to a movement of rotation, such as the therapeutic treatment of a patient by irradiation of part of his/her organism.

Another drawback of the known irradiation devices lies in the necessity to have access to the interior of the apparatus in order to change the light source or the radioactive source.

Finally, the irradiation apparatus of known type, using radioactive sources, have another important drawback—these radioactive sources must be changed when they have lost a determined quantity of their activity, in the course of time. In particular, when these apparatus are used in radiotherapy, their use must be suspended and a specialised team must be called upon to change these sources in situ with suitable equipment.

In addition, for certain applications such as the therapeutic treatment of a patient, a beam of photons of precise dimensions must be produced and the position of this beam must be adjusted. The irradiation devices of known type, which comprise an optical system illuminating over a solid angle of $4\pi$ steradians, do not allow a precise simulation of the beam of photons.

It is precisely an object of the present invention to provide a device for storing a source of photons and for irradiating a body by the radiation from said source, which overcomes the drawbacks of the devices of the prior art.

One object of the present invention is an irradiation device adapted to deliver a beam of photons of precise dimensions, which is easily adjustable, with a device ensuring a first collimation.

Another object of this invention is to provide a device enabling the radioactive sources to be changed without necessitating delicate manipulations on the site where the apparatus is used.

The irradiation device according to the present invention remedies these drawbacks, in that it serves both as storage device and as irradiation device. The radioactive source is placed in position inside the support disc; it is adjusted at the moment of manufacture. The device provided with its already-adjusted source is then transported onto the site of use. It then suffices to removably mount it, for example by means of screws, on a support arm, for it to be ready to operate without any additional adjustment. When, after a determined time, the activity of the radioactive source has decreased and it has become necessary to replace it, the irradiation device is dismantled from its support arm, and an identical irradiation device comprising a new source is mounted in its place. Specialised man-power for changing the source is thus unnecessary.

More precisely, the device for storing a source of photons and for irradiating a body by the radiation from said source is characterised in that it comprises:

a body for biological protection provided with a cylindrical cavity of circular section and two so-called first and second passages respectively, these passages opening at one and the other of their ends in said cavity and on the outer wall of the body, a disc for biological protection, whose shape is complementary of that of the cavity of the body and presenting, on the one hand, a housing centred on an axis perpendicular to the axis of the cavity, this housing opening out on the side wall of the disc, a source of γ radiation contained in said housing, a precollimator disposed at right angles to said first passage, means for rotating said disc between a first position for which said source is opposite the precollimator and a second position for which the source is in stored position.

This device has the following advantages:

due to its compactness, it may easily be mounted on its support in operational position, and due to the presence of a self-sufficient integrated biological protection, may be used directly for transporting radioactive sources, this biological protection being partly constituted by depleted uranium. This function of storage of the source makes it possible to avoid all operations of charging or discharging of the source on the site of use;

it is of small dimensions, whilst ensuring a good biological protection and opposing direct or diffused leaks of radiation, due to the use of a rotating disc for positioning the source of photons;

it is removable, and may easily be dismantled from its support arm;

finally, the use of depleted uranium, whose capacity of absorption of the radiation is greater than that of lead, for producing the biological protection, makes it possible to reduce the weight of this device. In particular, this reduces the unbalance thereof when it is mounted on a support arm animated by a movement of rotation.

For certain applications, it is necessary to deliver a light beam of precise dimensions, which is easily adjustable, serving to locate the beam of irradiation. For such applications, the biological protection disc of the storage device according to the invention further presents a passage disposed in the plane of the disc containing the axis of said housing, this passage opening at one and the other of its ends in two zones of the side wall of the disc capable of being simultaneously opposite said first and second passages;

at least one optical fibre disposed in said passage in the disc, the ends of said fibre, respectively called receiver and emitter ends, being held at right angles to each of the ends of said passage via dismountable fixing means;

an optical device fast with said body to produce a ray of light on the receiver end of said fibre, this device being disposed at right angles to said second passage.

This preferred arrangement allows a perfect simulation of the beam of photons due to the use of the emitter end of the optical fibre which may be defined and positioned with precision; it also allows the easy replacement of the optical device adapted to produce the ray of light on the receiver end of the optical fibre.

The irradiation device according to the invention also makes it possible, when the source is in stored position, to have access to each of the ends of the optical fibre via the passage of the body to which the optical device is disposed at right angles, whilst limiting the fixed positions of the biological protection disc to two. Thus, after the optical device has been dismantled, it is easy to introduce or remove the optical fibre in the short passage of the disc, and to adjust its positioning at right angles to the ends of said passage.

According to a preferred arrangement of the invention, the axes of the receiver and emitter ends of the fibre define an angle close to 90°. This arrangement enables the irradiation of the optical fibre in the course of functioning of the apparatus to be minimum.

According to another preferred embodiment of the invention, the angle of rotation of the protection disc, when the source passes from the storage position to the position of irradiation, is 110°. This arrangement limits the rate of leakage of the radiation from the source, when this latter is in storage position. It also enables the height of the protection body surrounding the disc to be limited.

According to the invention, the device for storing a source of photons and for irradiating a body by the radiation from said source, preferably comprises on the one hand electric means for locking the disc in said first position allowing irradiation, and on the other hand mechanical means for automatically placing the disc in said second position corresponding to the storage of the source.

Furthermore, the body is preferably constituted by a mass in which is included a block of depleted uranium, this block defining the portion of the wall of the cavity located around said source when said disc is in the storage position.

An important advantage of the invention is that it allows a rapid replacement of the radioactive source.

To this end, the invention also relates to a process for the replacement and transport of a radioactive source. This process is characterised in that it comprises the following successive steps of:

transporting to its site of use an irradiation device provided with a new, previously adjusted source ready for use, the irradiation device acting as a radioprotection cask, dismantling the irradiation device carrying the worn-out source from the support arm on which it is fixed, mounting the irradiation device comprising the new, preadjusted radioactive source.

Thus, the delicate adjustment of the source is effected when the device is manufactured. The irradiation device comprising the worn-out source is easily dismantled then the new irradiation device is easily mounted, without necessitating any additional adjustment and consequently without having to call upon specialised man-power.

The invention will be more readily understood on reading the following description with reference to the following drawings, in which FIG. 1 schematically shows an example of installation of the irradiation device according to the invention.

FIG. 2 shows a transverse section of the storage and irradiation device according to the invention.

FIG. 3 shows a longitudinal section of this same device.

FIGS. 5 and 6 show in detail the system for return by force of the biological protection disc.

Figure 1:
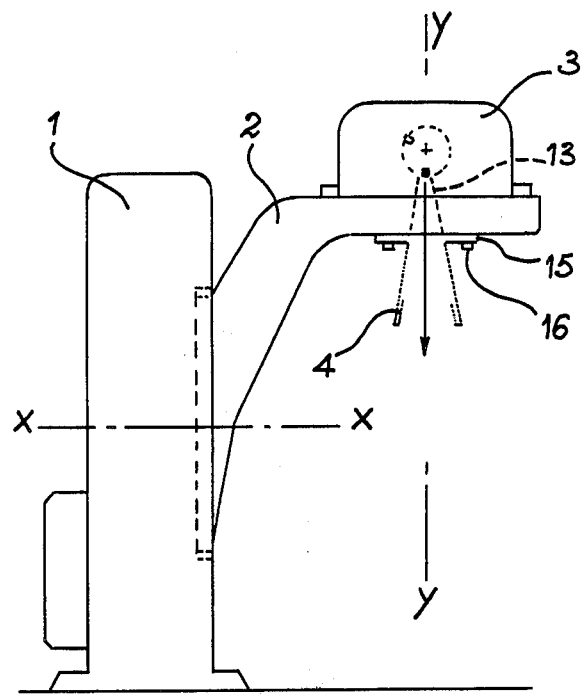

Referring now to the drawings, FIG. 1 shows an irradiation device which may advantageously be used in radiotherapy. This apparatus comprises a fixed support 1, an arm 2 movable about an axis X—X, an irradiation device 3 removably mounted on the mobile arm 2, a precollimator 13 and a secondary collimation device 4 of axis Y—Y. The collimator 4 is removably fixed on the mobile arm 2 by means of a support plate 15 fixed by screws 16.

FIG. 2 shows a transverse section through the irradiation device 3 of FIG. 1. This irradiation device comprises a bowl-shaped container 5 provided with a flange 6. This container 5 may be removably fixed on the arm 2 by means of screws passing through said flange 6.

A fixed shielding 7 for biological protection is placed inside the container 5. The shielding 7 at least partly surrounds a biological protection disc 8 rotatable about an axis passing through its centre C. The disc 8 is provided with a housing 9 adapted to receive a radioactive source. This housing 9 opens outwardly of the disc 8 so as to allow the beam of photons delivered by the radioactive source 10 to pass. The fixed shielding 7 is composed of a block 7a of depleted uranium, embedded in a block 7b of lead. The block 7a of depleted uranium surrounds the source of photons when the latter is in storage position shown in dashed and dotted lines in FIG. 2. The capacity of the uranium to absorb the radiation being about twice that of lead, the use of a block of depleted uranium ensures a satisfactory biological protection, whilst reducing the weight and size of the irradiation device according to the invention.

In the embodiment shown in FIG. 2, an optical fibre 11, adapted to transmit a light flux, is disposed in the disc 8. The optical fibre 11 opens at one of its ends 11a, so-called receiver end, opposite a light source 12 fixed outside the container 5 and at its other end 11b, called emitter and, along axis Y—Y. Each of the receiver and emitter ends is held via means for adjusting their positioning. The optical device 12 focuses a ray of light on the receiver end of the optical fibre 11, this optical device 12 consisting for example of a light source associated with a reflector for focusing its light beam. Light ray should be understood in the present specification to mean an electromagnetic radiation in the visible part of the spectrum.

The passage provided in the disc 8 for the optical fibre 11 is substantially rectilinear in shape, except for its ends. The emitter and receiver ends of the fibre 11 preferably determine an angle at the centre equal to 90°. Such an arrangement renders the irradiation of the optical fibre in the course of functioning of the apparatus minimum. In FIG. 2, $\alpha$ designates the angle of rotation of the disc 8 which makes it possible to pass from the position of irradiation of the radioactive source 10 shown in solid lines, to the storage position of this same source, shown in dashed and dotted lines. The value of this angle $\alpha$ is 110°. This value makes it possible to limit the rate of radiation leaks when the radioactive source 10 is in storage position, as well as the height of the biological protection body 7 surrounding the disc 8.

FIG. 3 shows a longitudinal section through the irradiation device shown in FIG. 2. This view particularly shows the positionings of the disc 8 ensuring a rapid alternance of the positions of irradiation and of storage, with locking of the disc in position of irradiation and return thereof into storage position in case of a safety action or an electrical failure.

The disc 8, mounted on bearings 15, rotates with the shaft 16. A clutch disc 18 is mounted at the end of the shaft 16. A pinion 20, mounted to rotate freely on the shaft 16, may be coupled to this shaft by means of the electromagnetic clutch 22. When the electromagnetic clutch 22 is supplied, the shaft 16 is rotated by the pinion 24 of the gear-down motor 26. On the other hand, the shaft 16 rotates, for example by means of a keying, with a pinion 30 driving a rack 32 which is intended to define the positions of irradiation and of storage of the disc 8.

Also shown schematically in dashed and dotted lines is the mobile arm 2 on which the device of the invention is mounted, as well as the device for maintaining the position of the disc 8, designated by reference 36 and, finally, the device 38 for displaying the position of the disc. These devices will be described in greater detail with reference to FIGS. 4, 5 and 6.

Figure 4B:
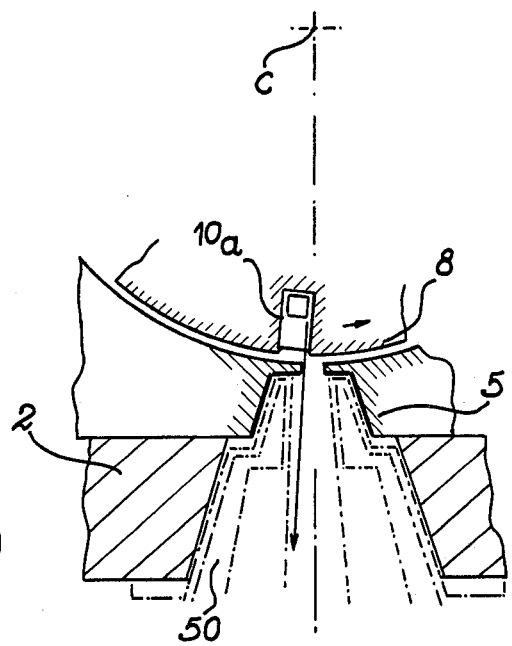
FIG. 4b shows a detailed view of the precollimation device.
Figure 4A:
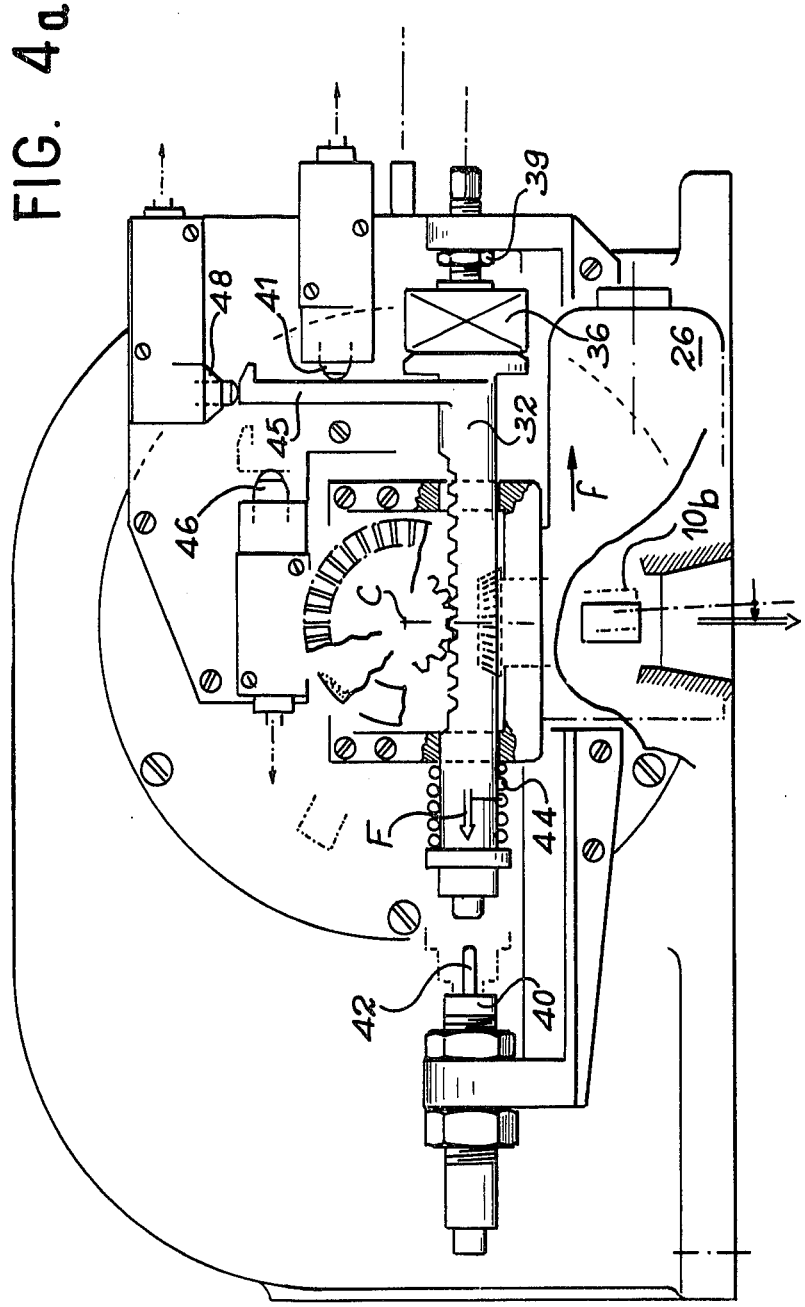
FIG. 4a shows a view in the direction IV of FIG. 3.

FIG. 4a shows a view in the direction of arrow IV of FIG. 3 of the device shown therein. This Figure particularly shows the device 41 for detecting the position of the disc 8.

The rack 32 may be displaced by a gear-down motor between a first position, shown in solid lines in FIG. 4a, for which it is in abutment against an electro-magnetic suction member 36 whose position is adjustable by means of a nut 39, and a second position, shown in dashed and dotted lines in FIG. 4a, for which the rack 32 is in the vicinity of a buffer unit 40 whose action is adjusted by the positioning of rod 42.

An electrical contact 41 controls the stoppage of the electro-magnetic clutch 22, when the rack 32, by being displaced in the direction of arrow f, comes to a short distance from the electro-magnetic member 36. Furthermore, to allow the disc 8 to return automatically into storage position, a spring 44 is interposed between a wall of the rack 32 and a fixed wall fast with the container 5, so that the disc automatically passes in the direction of arrow F from the position of irradiation to the position of storage if a safety device is triggered off or if there is an electrical failure.

A second electrical contact 46 actuated by finger 45 enables the end-of-stroke position of the rack 32 when it is in the vicinity of the buffer device 40 to be determined.

Finally, a third electrical contact 48 enables the beginning of irradiation to be determined. In fact, the beginning of irradiation is determined by the moment when the radioactive source 10 begins to appear in the precollimator. This position of the source, designated by reference 10a, has been shown in FIG. 4b.

Finally, FIG. 4a shows in dashed and dotted lines a second position 10b of the radioactive source, which corresponds to the radioactive source 10 going slightly beyond the position of the axis Y—Y of the collimation device. The purpose of this arrangement is to allow compensation of the inevitable clearance of the rack and drive pinion.

In FIG. 4b, reference 5 represents the precollimation device with, in addition, shown in dashed and dotted lines, a secondary collimation device 50 associated with the irradiation head.

FIGS. 5 and 6 show in detail the system allowing the return by force of the disc 8 in the case of incident. This device, generally designated by reference 38, is composed of a dog 60 made fast with the shaft 16 by means of a keying. The dog 60 bears a dog finger 62. The rotation of the dog 60 is limited by two stops 64 and 66. The stop 64, which is made of rubber, corresponds to irradiation position. The stop 66 corresponds to the position of storage of the radioactive source 10. Furthermore, a disc 68 is fast with the dog 60. The disc 68 comprises coloured zones corresponding to the different positions of the disc. Zone 68a corresponding to storage position is green and zone 68c corresponding to the position of irradiation is red.

A lever 70, whose angular movement is limited, is idly mounted on the end of the shaft 16. This lever allows the control by force of the disc 8 by means of the dog 60. It will be noted that the shaft 16 can be driven by this device only in one direction, this direction corresponding to the passage from the position of irradiation to the position of storage.

FIG. 5 shows in dashed and dotted lines the positions 70a and 70b of the lever 70 which correspond respectively to the positions of irradiation and of storage. An outer indexing means 72 located opposite the disc 68 makes it possible to determine the position of this disc due to the coloured zones thereof.

The irradiation device which has just been described has the important advantage of also serving as radioprotection cask for transporting the radioactive source. This makes it possible to adjust the source in the factory, at the moment of manufacture and to change the radioactive source simply, without calling upon specialised man-power. To this end, an irradiation device provided with a previously adjusted new source, ready for use, is transported to the site of use, the irradiation device acting as a radioprotection cask.

What is claimed is:

1. A photon storing and irradiation device having a radiation shielded body comprising a cylindrical container of circular cross section, having an axis (A), in said body; a disk housing located in said cylindrical container, dimensioned slightly smaller than that of said cylindrical container; a cylindrical gamma radiation containing housing in said disk, said housing having an opening on the periphery of the disk, with an axis perpendicular to axis (A) when the disk is rotated inside said body; said disk also containing a passage having an opening at one and the other of its ends at the periphery of the disk and capable of being located simultaneously opposite an optical device and a precollimator located in the walls of said cylindrical container and connected by an optical fiber, the ends of which, respectively called the receiver and emitter are located at right angles to each end of said passage via dismountable fixing means, and also having an optical device adjacent said body capable of producing a ray of light onto the receiver of said fiber; means for rotating said disk between a first position enabling said housing to irradiate a desired object for which the axis of said housing axis coincides with the axis (Y,Y) of the precollimator, and a second position for which said irradiation source is in a stored position while enabling the optical device by means of the optical fiber to produce a ray of light at the precollimator; and a part having an axis (Y,Y) perpendicular to axis (A) in the bottom of said body with said precollimator disposed at right angles to said port of axis (Y,Y).

2. The device of claim 1, wherein the axis of the receiver and emitter ends of the optical fiber define an angle close to 90°.

3. The device of claim 1, comprising electrical means for locking the disk in said first position.

4. The device of claim 1, wherein the disk is made of sintered tungsten.

5. The device of claim 1, wherein the body is constituted by a mass of lead in which is included a block of depleted uranium, this block defining the portion of the wall of the cavity located around said source when said disk is in said second position.

6. The device of claim 1, wherein the container of the irradiation head comprising the precollimator is provided with flanges for temporarily fixing it, by means of screws, on the movable arm of the support.

7. The device of claim 1, comprising mechanical means for automatically placing the disk in said first position.

8. The device of claim 7, wherein means for displacing said disk comprise a shaft coupled, on the one hand, to a geardown motor via an electromagnetic clutch and, on the other hand, to a rack movable between two end positions corresponding respectively to said first and second positions of the disk.

9. The device of claim 8, wherein the end position of the rack corresponding to said second position of the disk is defined by an electromagnetic stop adapted to lock the rack, this stop acting against a spring adapted to return the rack into an end position defined by a mechanical stop.

* * * * *